US00PP20131P2

(12) United States Plant Patent
Koppe

(10) Patent No.: US PP20,131 P2
(45) Date of Patent: Jun. 30, 2009

(54) ***BEGONIA* PLANT NAMED 'BORIASKO DARK'**

(50) Latin Name: *Begonia×hiemalis*
Varietal Denomination: Boriasko Dark

(75) Inventor: Lubbertus H. Koppe, Putten (NL)

(73) Assignee: Koppe Royalty B.V., Ermelo (NL)

( * ) Notice: Subject to any disclaimer, the term of this patent is extended or adjusted under 35 U.S.C. 154(b) by 0 days.

(21) Appl. No.: 12/077,207

(22) Filed: Mar. 17, 2008

(51) Int. Cl.
*A01H 5/00* (2006.01)

(52) U.S. Cl. ..... Plt./349
(58) Field of Classification Search ..... Plt./349
See application file for complete search history.

*Primary Examiner*—S. B McCormick Ewoldt
(74) *Attorney, Agent, or Firm*—C. A. Whealy

(57) ABSTRACT

A new and distinct cultivar of *Begonia* plant named 'Boriasko Dark', characterized by its upright and mounded plant habit; freely branching habit; double flowers that are light red in color and held above and beyond the foliage; and excellent postproduction longevity.

2 Drawing Sheets

Botanical designation: *Begonia×hiemalis.*
Cultivar denomination: 'Boriasko Dark'.

BACKGROUND OF THE INVENTION

The present invention relates to a new and distinct cultivar of *Begonia* plant, botanically known as *Begonia×hiemalis,* commercially known as Elatior *Begonia* and hereinafter referred to by the name 'Boriasko Dark'.

The new *Begonia* is a naturally-occurring whole plant mutation of the *Begonia×hiemalis* cultivar Boriasko, disclosed in U.S. Plant Pat. No. 14,589. The new *Begonia* was discovered and selected by the Inventor as a flowering plant from within a population of plants of the parent cultivar in a controlled greenhouse environment in Ermelo, The Netherlands in May, 2005.

Asexual reproduction of the new *Begonia* by cuttings taken in a controlled greenhouse environment in Ermelo, the Netherlands since July, 2005, has shown that the unique features of this new *Begonia* are stable and reproduced true to type in successive generations.

SUMMARY OF THE INVENTION

The cultivar Boriasko Dark has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Boriasko Dark'. These characteristics in combination distinguish 'Boriasko Dark' as a new and distinct *Begonia:*

1. Upright and mounded plant habit.
2. Freely branching habit.
3. Double flowers that are light red in color and held above and beyond the foliage.
4. Excellent postproduction longevity.

Plants of the new *Begonia* differ primarily from plants of the parent, the cultivar Boriasko, in flower color as plants of the cultivar Boriasko have light red and pink-colored flowers.

Plants of the new *Begonia* can also be compared to plants of the cultivar Barkos, disclosed in U.S. Plant Pat. No. 9,523. In side-by-side comparisons conducted in Ermelo, The Netherlands, plants of the new *Begonia* differed primarily from plants of the cultivar Barkos in flower color as plants of the cultivar Barkos had darker red-colored flowers.

BRIEF DESCRIPTION OF THE PHOTOGRAPHS

The accompanying colored photographs illustrate the overall appearance of the new *Begonia,* showing the colors as true as it is reasonably possible to obtain in colored reproductions of this type. Colors in the photographs may differ slightly from the color values cited in the detailed botanical description which accurately describe the colors of the new *Begonia.*

The photograph on the first sheet comprises a side perspective view of a typical flowering plant of 'Boriasko Dark' grown in a container.

The photograph on the second sheet is a close up view of upper and lower surfaces of typical leaves (left) and upper, side and lower surfaces of typical flowers (right) of 'Boriasko Dark'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in Ermelo, The Netherlands, under commercial practice in a glass-covered greenhouse during the winter. Average day and night temperatures were 20° C. during the first three to four weeks then lowered to an average day and night temperature of 18° C. until flowering. Four weeks after planting rooted cuttings in 13-cm containers, two five-day periods of long nyctoperiods of 16 hours were given and were separated by two days and subsequently followed by short nyctoperiods of eight hours until flowering. Plants were pinched one time about one week after planting. Plants were about 14 weeks from planting when the photographs and description were taken.

Botanical classification: *Begonia×hiemalis* cultivar Boriasko Dark.

Commercial classification: Elatior *Begonia*.

Parentage: Naturally-occurring whole plant mutation of the *Begonia×hiemalis* cultivar Boriasko, disclosed in U.S. Plant Pat. No. 14,589.

Propagation:

*Type.*—By terminal vegetative cuttings.

*Time to develop roots.*—About 20 days at temperatures 20° C.

*Time to produce a rooted young plant.*—About five weeks at temperatures of 20° C.

*Root description.*—Fine, fibrous, well-branched; white/orange in color. Plants of the new *Begonia* have not been observed to form tubers.

Plant description:

*Plant form.*—Compact, upright and mounded plant habit, inverted triangle; freely branching with good stem and stem base strength. Flowers are double and abundant. Plants flower continuously.

*Growth habit.*—Vigorous growth habit; suitable for 12 to 15-cm containers. Under optimal environmental and cultural conditions, usually about 14 weeks are required to produce proportional 13-cm potted plants from cuttings. Vegetative shoots are formed at basal nodes and flowering shoots are formed at upper nodes.

*Plant height.*—About 30 cm.

*Plant width.*—About 38 cm.

*Leaves.*—Arrangement: Simple, alternate. Developing leaves, length: About 7.5 cm. Developing leaves, width: About 7.5 cm. Fully expanded leaves, length: About 16 cm. Fully expanded leaves, width: About 13 cm. Shape: Roughly reniform. Apex: Acuminate to acute. Base: Cordate; oblique. Margin: Doubly serrate. Texture, upper and lower surfaces: Smooth, glabrous. Venation pattern: Palmate. Color: Developing leaves, upper surface: Darker than 147A. Developing leaves, lower surface: Close to 147B. Fully expanded leaves, upper surface: Much darker than between 147A and N189A; venation, 146A to 146B. Fully expanded leaves, lower surface: Close to between 147B and 191A; venation, 146C. Petiole length: About 2 cm to 7 cm. Petiole texture, upper and lower surfaces: Slightly pubescent. Petiole color, upper and lower surfaces: Close to 146D; with development, color becoming closer to 174B.

Flower description:

*Flowering habit.*—Double flowers with numerous tepals arranged in axillary cymes. Usually five to nine flowers per cyme. Many cymes in flower simultaneously. Flowers positioned above and beyond the foliage. Flowering continuous.

*Natural flowering season.*—Plants will flower year round regardless of nyctoperiod, however plants flower earlier and more abundantly from mid-February until November in the Northern Hemisphere.

*Flowers.*—Shape: Rounded; rose-like. Diameter: About 6 cm. Depth (height): About 2 cm.

*Flower buds.*—Length: About 1 cm to 2 cm. Diameter: About 1 cm to 2.2 cm. Color: Close to 46A.

*Tepals.*—Arrangement: Rosette. Quantity per flower: Usually about 35 per flower. Size: Outer tepals, length: About 3 cm to 3.5 cm. Outer tepals, width: About 3.8 cm. Inner tepals, length: About 1.1 cm to 2.8 cm. Inner tepals, width: About 1.3 cm to 2.8 cm. Shape: Rounded flabellate. Apex: Rounded to truncate. Margin: Slightly crenate. Texture, upper and lower surfaces: Smooth, glabrous; satiny. Color: When opening, upper surface: Close to 46C to 46D; towards the margins, fading to lighter than 46D. When opening, lower surface: Close to 47B to 47C. Fully opened, upper surface: Close to 52A; towards the margins, fading to 54D. Fully opened, lower surface: Close to 46D; towards the margins, 54D.

*Flower bracts.*—Quantity/arrangement: Two, opposite. Shape: Broadly ovate. Apex: Acute. Margin: Serrate. Texture, upper and lower surfaces: Glabrous, smooth. Color, upper and lower surfaces: Close to 146C to 146D.

*Peduncles.*—Angle: Erect. Length: About 6.5 cm to 8 cm. Texture: Slightly pubescent. Color: Close to 146C.

*Pedicels.*—Angle: Erect. Length: About 2.4 cm to 4.4 cm. Texture: Slightly pubescent. Color: Between 146C and 166B to 166C.

*Reproductive organs.*—Stamens: None observed. Pistils: None observed.

*Seed/fruit.*—Seed and fruit production have not been observed as reproductive organs are not formed.

Postproduction longevity: Individual flowers: Generally about two to three weeks. Whole plants: About seven weeks under interior conditions.

Disease/pest resistance: Resistance to pathogens and pests common to *Begonia* has not been observed.

Temperature tolerance: Plants of the new *Begonia* have been observed to tolerate temperatures from about 10° C. to about 35° C.

It is claimed:

1. A new and distinct *Begonia* plant named 'Boriasko Dark' as illustrated and described.

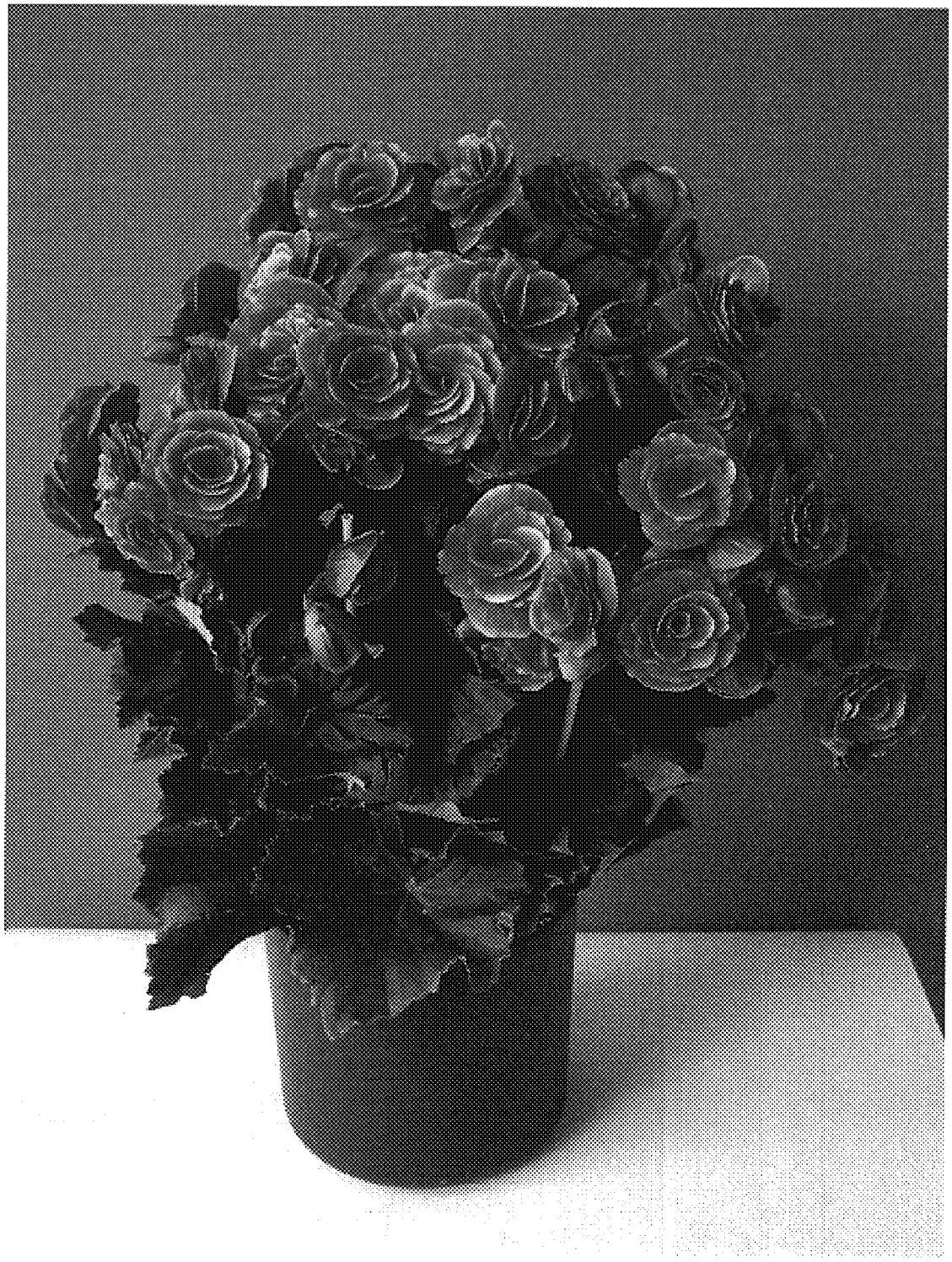

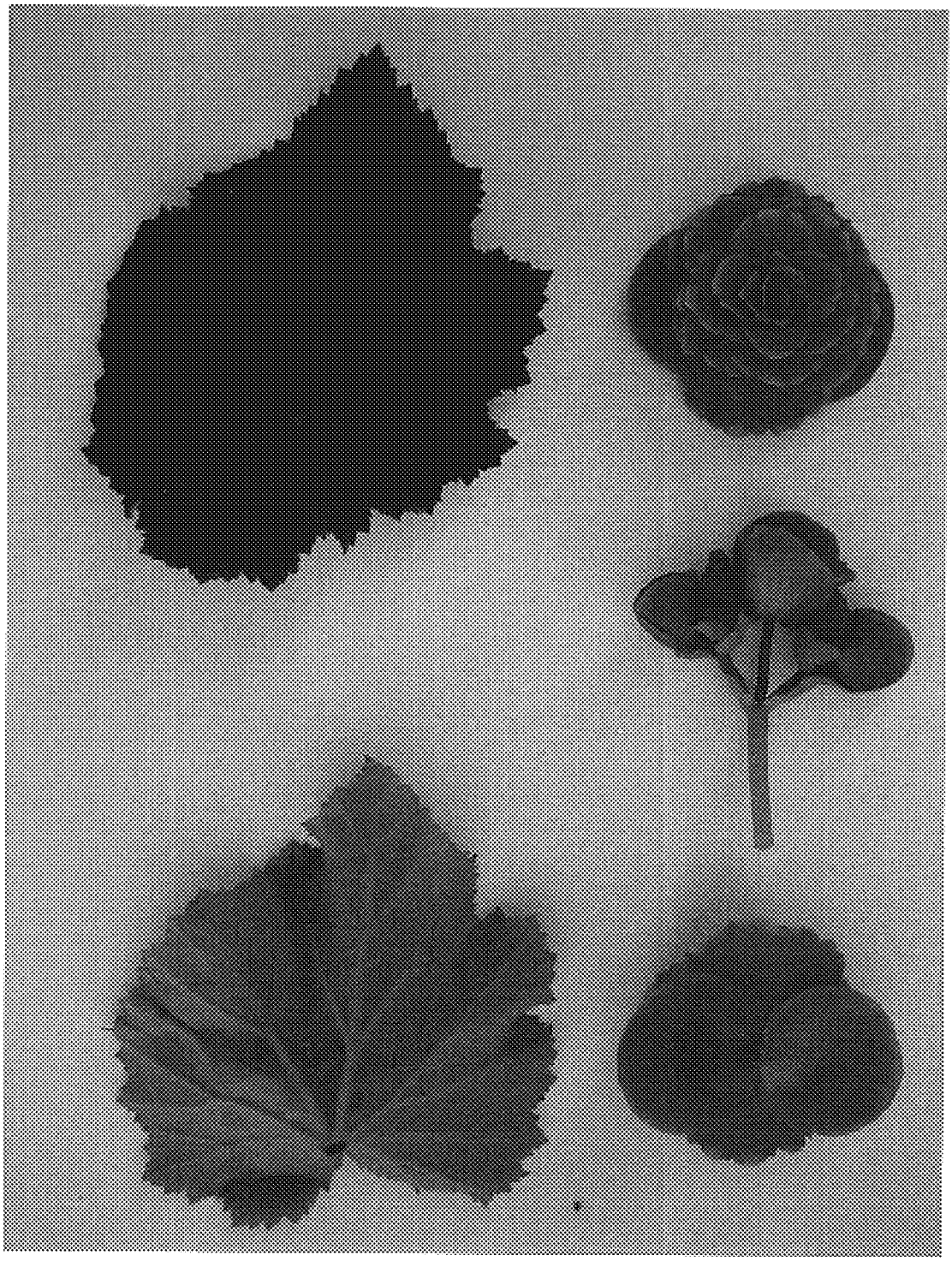

* * * * *